United States Patent
Kim et al.

(10) Patent No.: US 10,211,487 B2
(45) Date of Patent: Feb. 19, 2019

(54) METHOD FOR PREDICTING BATTERY HEALTH IN CONSIDERATION OF TEMPERATURE OF BATTERY MANAGEMENT SYSTEM

(71) Applicant: Korea University of Technology and Education Industry-University Cooperation Foundation, Cheonan-si, Chungcheongnam-do (KR)

(72) Inventors: Kwangsun Kim, Cheonan-si (KR); Junyoung Kim, Hwaseong-si (KR); Kangwo Joo, Cheonan-si (KR)

(73) Assignee: Korea University of Technology and Education Industry-University Cooperation Foundation, Cheonan-si (KR)

( * ) Notice: Subject to any disclaimer, the term of this patent is extended or adjusted under 35 U.S.C. 154(b) by 165 days.

(21) Appl. No.: 15/359,099

(22) Filed: Nov. 22, 2016

(65) Prior Publication Data

US 2018/0123185 A1    May 3, 2018

(30) Foreign Application Priority Data

Oct. 31, 2016  (KR) .......................... 10-2016-0142709

(51) Int. Cl.
*H01M 10/44* (2006.01)
*G01N 25/00* (2006.01)
(Continued)

(52) U.S. Cl.
CPC .......... *H01M 10/443* (2013.01); *G01N 25/00* (2013.01); *G01R 31/3648* (2013.01);
(Continued)

(58) Field of Classification Search
CPC ............... G01N 25/00; G01R 31/3648; G01R 31/3679; G01R 31/44; H01M 10/443;
(Continued)

(56) References Cited

U.S. PATENT DOCUMENTS

2014/0370940 A1* 12/2014 Yoshida .............. H01M 10/425
455/572
2015/0369873 A1* 12/2015 Nakao ................ G01R 31/3606
702/63

FOREIGN PATENT DOCUMENTS

JP    2000-243459 A    9/2000
JP    2007-010370 A    1/2007
(Continued)

*Primary Examiner* — Kyle R Quigley
(74) *Attorney, Agent, or Firm* — Novick, Kim & Lee, PLLC; Jae Youn Kim

(57) ABSTRACT

Provided is a method for predicting battery health in consideration of a temperature of a battery management system, the method including: measuring the voltage, current, and temperature of the battery and calculating the initial state of charge (SOC) of the battery by an internal control unit when the operation of the battery management system (BMS) is started; checking whether the battery is in the charged state or in the discharged state by the control unit; calculating the current amount of accumulated discharge by the control unit if the battery is in the discharged state; calculating an accumulated discharge rate capacity by the control unit if the battery is in the charged state and if the amount of accumulated discharge is calculated; calculating the capacity reduction rate of the battery depending on the average usage temperature of the battery by the control unit; calculating a currently available battery capacity ratio by using the capacity reduction rate and the accumulated discharge rate capacity value by the control unit; and calculating and outputting the state of health (SOH) of the battery, which corresponds (Continued)

to the temperature change of the battery, by the control unit based on the battery capacity ratio.

4 Claims, 7 Drawing Sheets

(51) Int. Cl.
  *G01R 31/36* (2006.01)
  *H01M 10/48* (2006.01)
  *H02J 7/00* (2006.01)
  *H01M 10/42* (2006.01)
(52) U.S. Cl.
  CPC ...... *G01R 31/3679* (2013.01); *H01M 10/446* (2013.01); *H01M 10/48* (2013.01); *H01M 10/486* (2013.01); *H02J 7/0047* (2013.01); *H01M 2010/4271* (2013.01)
(58) Field of Classification Search
  CPC .. H01M 10/446; H01M 10/48; H01M 10/486; H01M 2010/4271; H02J 7/0047
  See application file for complete search history.

(56) References Cited

FOREIGN PATENT DOCUMENTS

| | | |
|---|---|---|
| JP | 2016-038240 A | 3/2016 |
| KR | 10-2007-0043150 A | 4/2007 |
| KR | 100766982 B1 | 10/2007 |

* cited by examiner

METHOD FOR PREDICTING BATTERY HEALTH IN CONSIDERATION OF TEMPERATURE OF BATTERY MANAGEMENT SYSTEM

CROSS-REFERENCE TO RELATED APPLICATION

This application claims priority to Korean Patent Application No. 10-2016-0142709 filed in the Korean Intellectual Property Office on Oct. 31, 2016, the entire contents of which are incorporated herein by reference.

BACKGROUND OF THE INVENTION

1. Field of the Invention

The present invention relates to a method for predicting battery health in consideration of the temperature of a battery management system, and more specifically, relates to a method for predicting battery health in consideration of the temperature of a battery management system, which enables the prediction of the state of health (SOH) of a battery in consideration of the usage temperature of the battery in the current usage environment of a rechargeable battery.

2. Description of the Prior Art

Recently, the use of a battery system is rapidly increasing in a variety of fields, and research and improvements on a battery management system (BMS) have been made according to the needs for careful monitoring and charging/discharging control in order to maintain the capacity, lifespan, and safety of the battery.

The battery management system (BMS), as shown in FIG. 1, monitors the voltage (V), current (I), or temperature (T) of a battery cell (or a battery pack) for monitoring and managing the state of health (SOH) and the state of charge (SOC) (or the current charged/discharged state of the battery) of the battery cell (or the battery pack).

For example, in all systems (for example, electric vehicles, smart phones, or the like) that use rechargeable batteries (for example, lithium ion batteries), when the battery is repeatedly charged and discharged (that is, when a cycle of charging/discharging is repeated), the performance thereof does not return to the original state (or the initial chargeable capacity) so that the charging and discharging time is reduced and the lifespan of the battery gradually decreases.

Accordingly, in various relevant industries where the rechargeable batteries are currently used, the current state of the battery is monitored in real time through the battery management system (BMS), and when the state of the battery reaches a certain level or less, the battery is replaced.

However, since a change in the performance (for example, the battery capacity) becomes severe and the lifespan of the battery is significantly affected in extreme environments (for example, at high or low temperature), the replacement time of the battery becomes incorrect. As a result, it causes an inconvenience in the operation of the battery.

Therefore, an improvement is required, which is able to more accurately predict the state of health (SOH) of the battery in consideration of the temperature in the current battery usage environment, in addition to the monitoring of the battery by using the battery management system (BMS), so that the user can be aware of the battery replacement timing in advance and can appropriately manage the battery.

The technical background of the present invention is disclosed in Korea Patent Publication No. 10-2007-0043150 (published on 25 Apr. 2007; Method for predicting SOC of battery and battery management system using the same).

SUMMARY OF THE INVENTION

According to an aspect of the invention, the present invention has been made to solve the problems above and has the objective of providing a method for predicting battery health in consideration of the temperature of the battery management system, which enables the prediction of the state of health (SOH) of the battery in consideration of the usage temperature of the battery in the current usage environment of the rechargeable battery.

A method for predicting battery health in consideration of a temperature of a battery management system, according to an aspect of the present invention, may include: measuring the voltage, current, and temperature of the battery and calculating the initial state of charge (SOC) of the battery by an internal control unit when the operation of the battery management system (BMS) is started; checking whether the battery is in the charged state or in the discharged state by the control unit; calculating the current amount of accumulated discharge by the control unit if the battery is in the discharged state; calculating an accumulated discharge rate capacity by the control unit if the battery is in the charged state and if the amount of accumulated discharge is calculated; calculating the capacity reduction rate of the battery depending on the average usage temperature of the battery by the control unit; calculating a currently available battery capacity ratio by using the capacity reduction rate and the accumulated discharge rate capacity value by the control unit; and calculating and outputting the state of health (SOH) of the battery, which corresponds to the temperature change of the battery, by the control unit based on the battery capacity ratio.

In the present invention, the initial state of charge (SOC) of the battery is calculated based on a relationship between the open circuit voltage (OCV) and the state of charge (SOC) according to the voltage stabilization time, and is calculated based on the voltage that is measured in the state after the lapse of the voltage stabilization time or in the initial state in which a load is not operated.

In the present invention, the voltage stabilization time refers to the time taken for a voltage change to be stable in the state in which the discharge of the battery is completely stopped, and is determined according to whether or not the voltage change value reaches a predetermined voltage change value or less.

In the present invention, the accumulated discharge rate capacity refers to a ratio of the current state of charge of the battery according to the amount of accumulated discharge to the initial state of charge of the battery, and is calculated by dividing the current state of charge of the battery according to the current amount of accumulated discharge by the initial state of charge of the battery.

In the present invention, the battery capacity ratio (y) to the accumulated discharge rate capacity is calculated by adding a first predetermined constant to a value that is obtained by multiplying a first coefficient that is calculated for each temperature and the accumulated discharge rate capacity (x) (y=−first coefficient*x+first constant).

In the present invention, the capacity reduction ratio (y) of the battery depending on the temperature is calculated by adding a second pre-calculated constant to a value that is obtained by multiplying a second pre-calculated coefficient and the temperature (x) (y=second coefficient*x+second constant).

In the present invention, when the initial value of the battery capacity ratio is set to be 100%, which is the maximum value of the state of health (SOH) of the battery, and when the amount of accumulated discharge corresponding to the current temperature (T) is C, the control unit may: calculate the amount of capacity reduction for each temperature by multiplying the capacity reduction rate of the battery according to the temperature and the amount of accumulated discharge (C) {capacity reduction amount= (second coefficient*T+second constant)*C}; calculate the first available amount of discharge (SOH) that is the remaining state of health of the battery by subtracting the amount of accumulated discharge reflecting the amount of capacity reduction for each temperature from the maximum battery state of health (SOH) of 100%; calculate the second available amount of discharge (SOH) by subtracting a predetermined reference available amount of discharge from the first available amount of discharge (SOH) that is calculated; apply the second available amount of discharge (SOH) to the equation {capacity reduction amount=(second coefficient*T+second constant)*C} for calculating the amount of capacity reduction; and calculate C that is calculated from the equation for calculating the amount of capacity reduction as the final available amount of discharge (SOH) that is the remaining state of health of the battery.

According to an aspect of the invention, the present invention enables the prediction of the state of health (SOH) of the battery in consideration of the usage temperature of the battery in the current usage environment of the rechargeable battery so that the user can be aware of the battery replacement timing in advance and can appropriately manage the same.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION OF THE EXEMPLARY EMBODIMENTS

Figure 1:
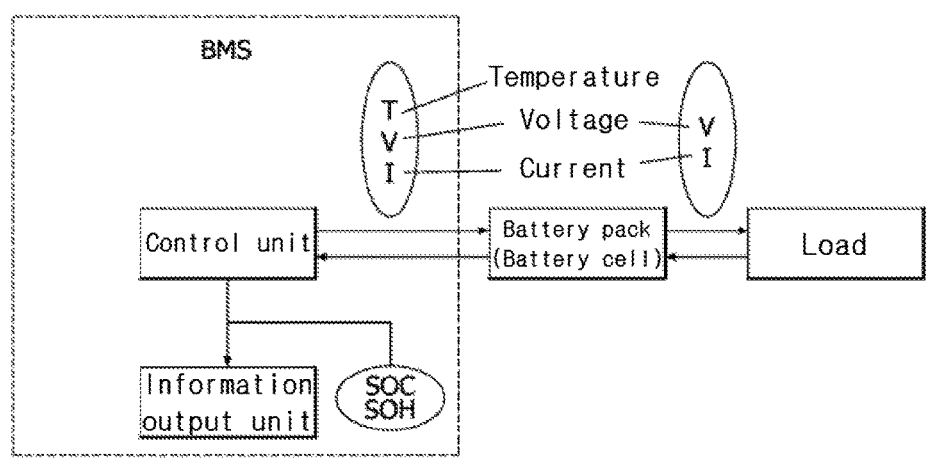
FIG. 1 is an exemplary view for explaining the operation of a typical battery management system.

Hereinafter, an embodiment of a method for predicting battery health in consideration of a temperature of a battery management system, according to the present invention, will be described with reference to the accompanying drawings.

In the course of description, the thicknesses of lines or the sizes of constituent elements shown in the drawings may be exaggerated for the clearness and convenience of description. The following terms are defined in consideration of their functions in the present invention, and may be changed according to an intention or customs of a user or a manager. Therefore, the definitions of the terms should be made based on the contents over the entire specification.

Figure 2:
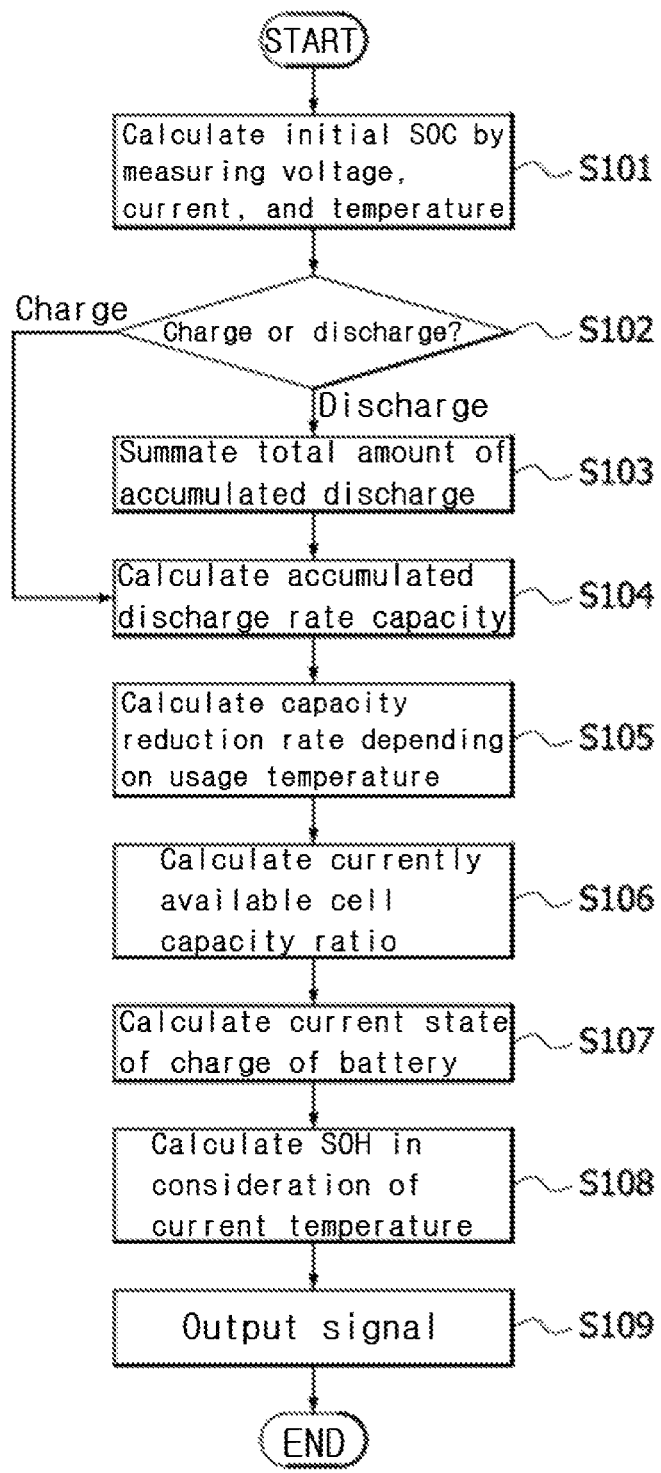
FIG. 2 is a flowchart for explaining a method for predicting the battery health in consideration of the temperature of the battery management system, according to an embodiment of the present invention.

FIG. 2 is a flowchart for explaining a method for predicting the battery health in consideration of the temperature of the battery management system, according to an embodiment of the present invention.

As shown in FIG. 2, the control unit (not shown) of the battery management system (BMS) that is related to the present embodiment measures the voltage, current, and temperature of a battery cell (or a battery pack) in order to thereby calculate the initial state of charge (SOC) (S101).

For reference, the control unit of the battery management system (BMS) (hereinafter, referred to as a control unit) measures the voltage, current, and temperature of the battery cell (or the battery pack) after the operation (i.e., the initialization) of the battery management system (BMS), and calculates the initial SOC based on a relationship between the open circuit voltage (OCV) and the state of charge (SOC) according to the voltage stabilization time from the time when it is turned off last.

In general, the actual state of charge (SOC) of the battery should be calculated by using the voltage (OCV; open circuit voltage) after the load applied to the battery is completely removed in order to accurately calculate the same. However, it is difficult to calculate the state of charge (SOC) of the battery by the open circuit voltage (OCV) in devices or systems (for example, electric vehicles, smart phones, or the like) that are in operation under the actual load.

Since it is difficult to calculate the state of charge (SOC) of the battery by the open circuit voltage (OCV) in devices or systems that are in operation under the actual load as described above, the state of charge (SOC) of the battery may be calculated by measuring the voltage after the elapse of the voltage stabilization time (for example, about 11 minutes) in the state in which the discharge of the battery is completely stopped (for example, in the state in which the operation of the device or system is stopped).

Figure 3:
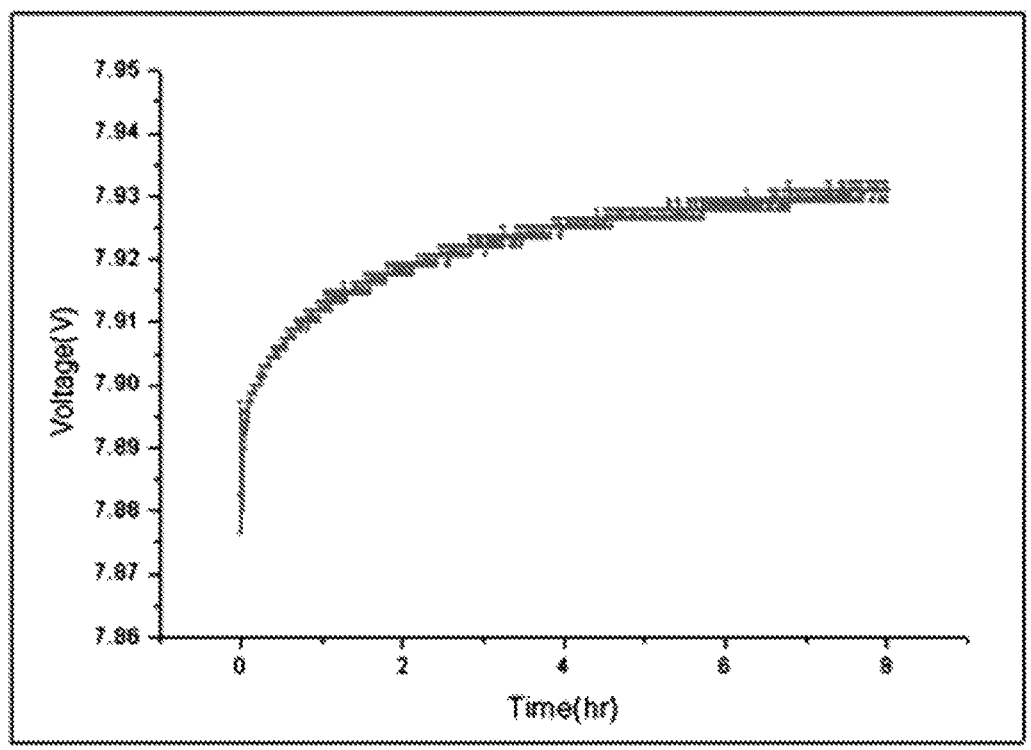
FIG. 3 is an exemplary view showing a graph of a voltage change that appears as the polarization is eliminated after the battery cell (or the battery pack) stops discharge, according to an embodiment of the present invention.

Here, the voltage stabilizing time (for example, about 11 minutes) refers to the time when a voltage change becomes stable in a state in which the discharge of the battery is completely stopped (for example, the voltage change may be determined to be stable when the voltage change is equal to, or less than, 0.02V) as shown in the graph of FIG. 3, and as a result of repeated tests, it can be seen that the voltage change becomes stable when about 11 minutes have elapsed since the stop of the battery discharge.

Therefore, the initial SOC based on a relationship between the open circuit voltage (OCV) and the state of charge (SOC) of the battery according to the voltage stabilization time refers to the SOC that is calculated based on the voltage that is measured in the state in which such a voltage as the open circuit voltage (OCV) can be measured (that is, in the state in which the voltage stabilization time has elapsed or in the initial state in which the load is not operated).

Here, FIG. 3 is an exemplary view showing a graph of a voltage change that appears as the polarization is eliminated after the battery cell (or the battery pack) stops discharge, according to an embodiment of the present invention. Referring to FIG. 3, it can be seen that it comes to the voltage stabilization state in which the voltage change is equal to, or less than, 0.02V after the lapse of the voltage stabilizing time (for example, about 11 minutes).

Figure 4:
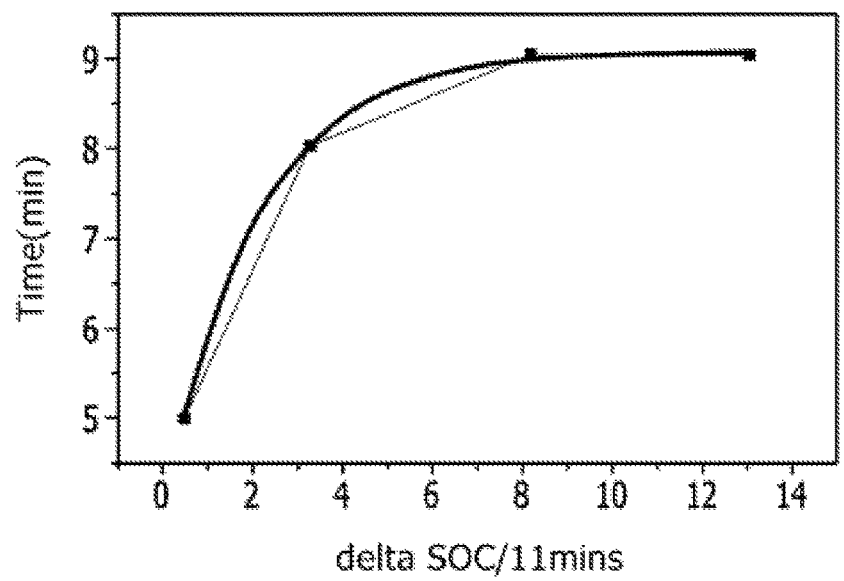
FIG. 4 is an exemplary view showing a test result of the voltage stabilization time depending on a change in the state of charge (SOC) of the battery, according to an embodiment of the present invention.

FIG. 4 is an exemplary view showing a test result of the voltage stabilization time depending on a change in the state of charge (SOC) of the battery, according to an embodiment of the present invention, which shows that the time required to reach the target state of charge (SOC) of the battery is measured to be the same (i.e., 11 minutes) within an error range as a result of testing the time to be taken until the voltage stabilization state with different states of charge (SOC) of the battery.

Figure 5:
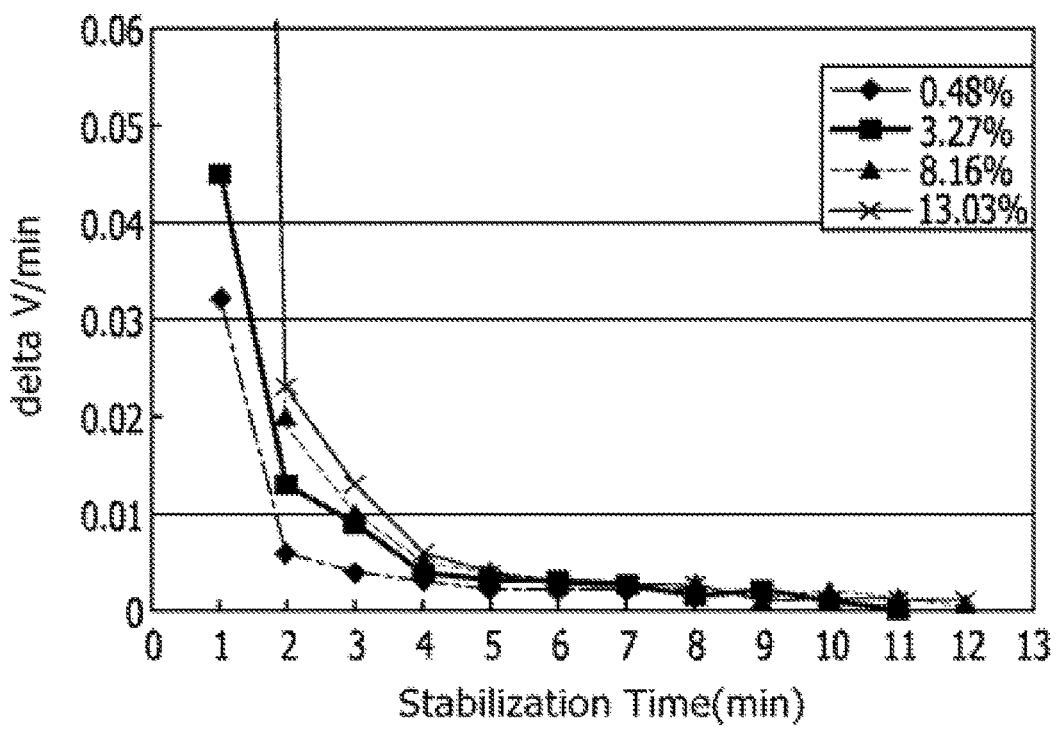
FIG. 5 is an exemplary view showing a regression analysis graph of the voltage stabilization time depending on a change in the state of charge (SOC) of the battery, according to an embodiment of the present invention.

FIG. 5 is an exemplary view showing a regression analysis graph of the voltage stabilization time depending on a change in the state of charge (SOC) of the battery, according to an embodiment of the present invention. That is, FIG. 5 is an exemplary view showing the result of a regression analysis of the voltage stabilization time depending on a change in the state of charge (SOC) of the battery based on the test result shown in the exemplary view of FIG. 4. Referring to FIG. 5, the degree (or pattern) of the voltage change depending on time after the stop of the battery discharge is gradually reduced to then be stabilized.

For example, referring to FIG. 5, it can be seen that: the voltage change is the maximum for about 2 minutes at an early stage after the battery discharge is stopped; the voltage change gradually decreases for about 3 minutes thereafter; and the voltage hardly changes to then be in the stabilization state 5 minutes to 11 minutes after the battery discharge is stopped.

Therefore, it can be seen that it is possible to calculate the state of charge (SOC) of the battery without waiting for the battery to come to the voltage stabilization state (or without waiting for the voltage stabilization time to elapse) based on the degree (or pattern) of the voltage change depending on time shown in the exemplary view of FIG. 5.

Figure 6:
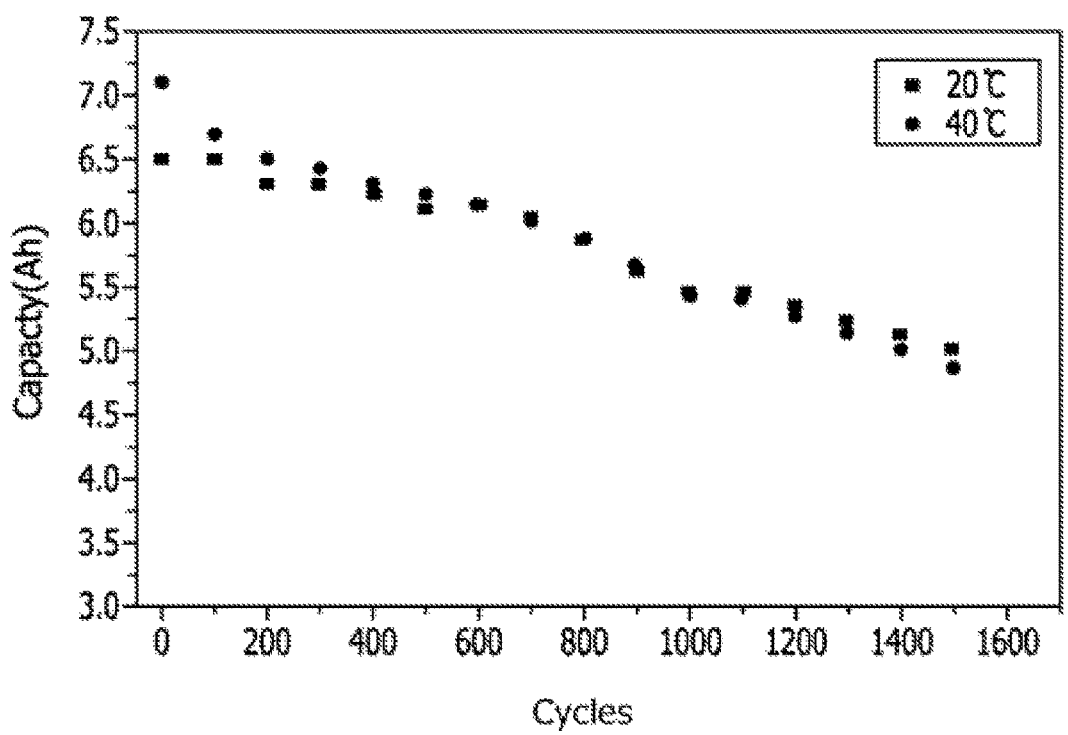
FIG. 6 is an exemplary view showing a change in the state of charge of the battery depending on an increase in the charging/discharging cycle of the battery that is related to an embodiment of the present invention.
Figure 7:
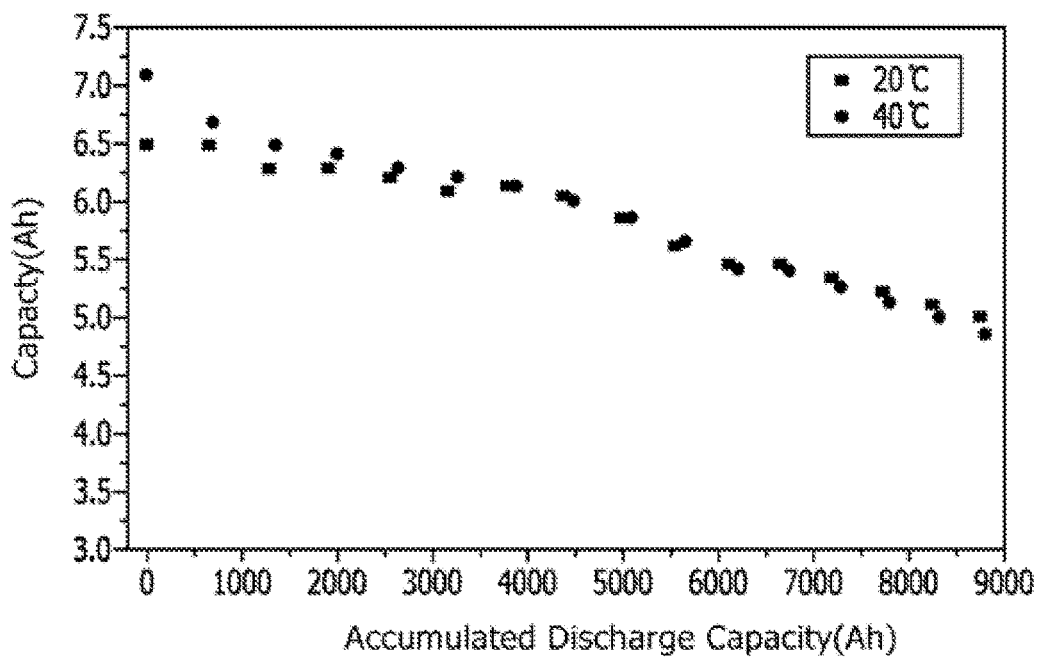
FIG. 7 is an exemplary view showing a change in the state of charge of the battery depending on the amount of accumulated discharge of the battery that is related to an embodiment of the present invention.

FIG. 6 is an exemplary view showing a change in the state of charge of the battery depending on an increase in the charging/discharging cycle of the battery that is related to an embodiment of the present invention, and FIG. 7 is an exemplary view showing a change in the state of charge of the battery depending on the amount of accumulated discharge of the battery that is related to an embodiment of the present invention.

Referring to FIG. 6, it can be seen that the state of charge of the battery decreases with an increase in the charging/discharging cycles (the number of times of charging/discharging) of the battery, and when performing the charging/discharging for about 1500 cycles (times), the state of charge of the battery decreases by approximately 50%.

Meanwhile, referring to FIG. 7, it can be seen that the state of charge of the battery decreases with an increase in the amount of accumulated discharge of the battery, wherein the state of charge of the battery decreases by approximately 50% when the amount of accumulated discharge reaches 9000 (Ah).

Here, one cycle means only the number of times of charging/discharging regardless of the discharge state of the battery, and the amount of accumulated discharge refers to a value that is obtained by accumulating the amount of discharge just before starting to charge the battery. That is, one cycle is counted to increase upon the start of the charging even in the state in which the battery is not completely discharged, whereas the amount of accumulated discharge is different from the same in its meaning because it refers to a value that is obtained by accumulating the amount of discharge before starting to charge the battery.

Referring back to FIG. 2, after calculating the initial SOC (S101), the control unit checks whether the battery is in the charged state or in the discharged state (S102).

If the battery is in the discharged state as a result of the checking (S102), the current amount of discharge is added to the amount of accumulated discharge (S103). That is, the amount of accumulated discharge including the current amount of discharge (that is, the amount of accumulated discharge is calculated, which is obtained by accumulating and storing the amount of discharge until the battery's life ends since it is released).

If the battery is in the charged state as a result of the checking (S102) and if the amount of accumulated discharge is calculated, the accumulated discharge rate capacity is calculated (S104).

Here, the accumulated discharge rate capacity means a ratio of the current state of charge of the battery according to the amount of accumulated discharge to the initial state of charge of the battery, and it is a factor to enable an accurate calculation of the state of charge of the battery (SOC) even if it is aged regardless of the capacity of the battery is large or small. At this time, the accumulated discharge rate capacity may be calculated by dividing the current state of charge of the battery according to the current amount of accumulated discharge by the initial state of charge of the battery.

Figure 8:
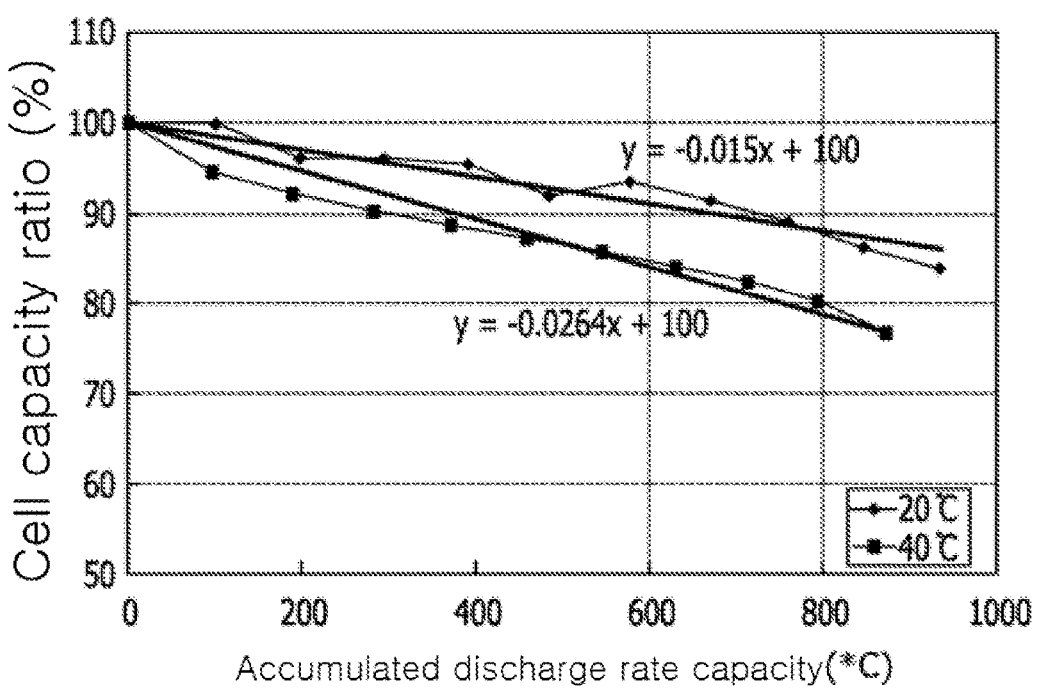
FIG. 8 is an exemplary view showing a graph for a test result of a change in the cell capacity ratio (%) with respect to the accumulated discharge rate capacity for each battery-usage temperature, according to an embodiment of the present invention.
Figure 9:
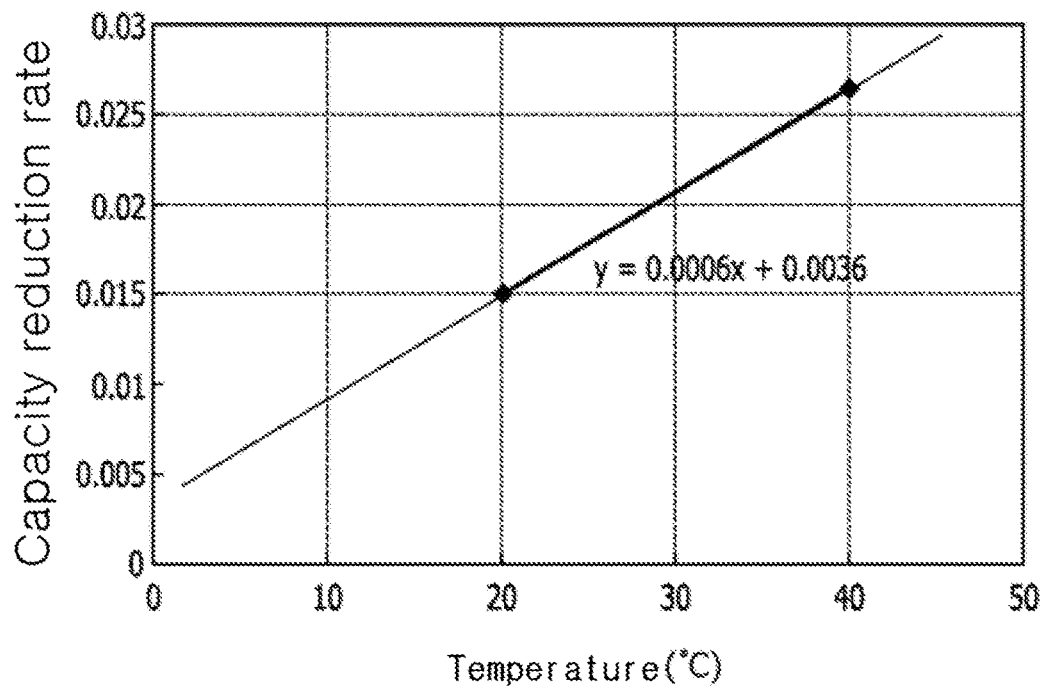
FIG. 9 is an exemplary view showing a graph of a capacity reduction rate of the battery depending on a change in the temperature, according to an embodiment of the present invention.

FIG. 8 is an exemplary view showing a graph for a test result of a change in the battery capacity ratio (or cell capacity ratio) (%) with respect to the accumulated discharge rate capacity for each battery-usage temperature, according to an embodiment of the present invention, and FIG. 9 is an exemplary view showing a graph of a capacity reduction rate of the battery depending on a change in the temperature, according to an embodiment of the present invention.

Referring to FIG. 8, the graph for a test result of a change in the battery capacity ratio (or cell capacity ratio) (%) with respect to the accumulated discharge rate capacity for each usage temperature may be converted to Equations 1 and 2 as follows.

$$20°\text{C.}: y=-0.015x+100 \quad \text{[Equation 1]}$$

$$40°\text{C.}: y=-0.026x+100 \quad \text{[Equation 2]}$$

Here, 0.015 and 0.026 denote coefficients that are calculated for each temperature, and y denotes the battery capacity ratio (or cell capacity ratio). x denotes the accumulated discharge rate capacity.

Based on Equations 1 and 2 above, a change in the capacity reduction rate of battery depending on a temperature change (that is, the degree by which the state of charge of the battery is reduced depending on a temperature change) may be calculated (see FIG. 9), which may be an evaluation index of the state of health (SOH) of the battery.

Referring to FIG. 9, as the usage temperature increases, the capacity reduction rate increases. The graph of the capacity reduction rate of the battery according to a change in the usage temperature may be converted to Equation 3 as follows.

$$y=0.0006x+0.0036 \quad \text{[Equation 3]}$$

Here, y refers to the capacity reduction ratio, and x refers to the temperature. The coefficient (0.0006) and the constant (0.0036) may be calculated through a regression analysis by repeated experiments.

The battery replacement time (that is, the battery replacement time according to a predetermined state of charge of the battery) may be predicted based on the capacity reduction rate depending on a temperature change (for example, the battery replacement time may be predicted by calculating the SOH by using Equation 4).

Referring back to FIG. 2, the control unit calculates the accumulated discharge rate capacity of the battery (S104), and then calculates the capacity reduction rate of the battery depending on the usage temperature (for example, an average usage temperature) of the battery (S105).

When the capacity reduction rate of the battery is calculated as described above, the control unit calculates a currently available battery capacity ratio (or cell capacity ratio) (%) by using the capacity reduction rate and the accumulated discharge ratio capacity value, which are calculated above (S106) (see FIG. 8).

Figure 10:
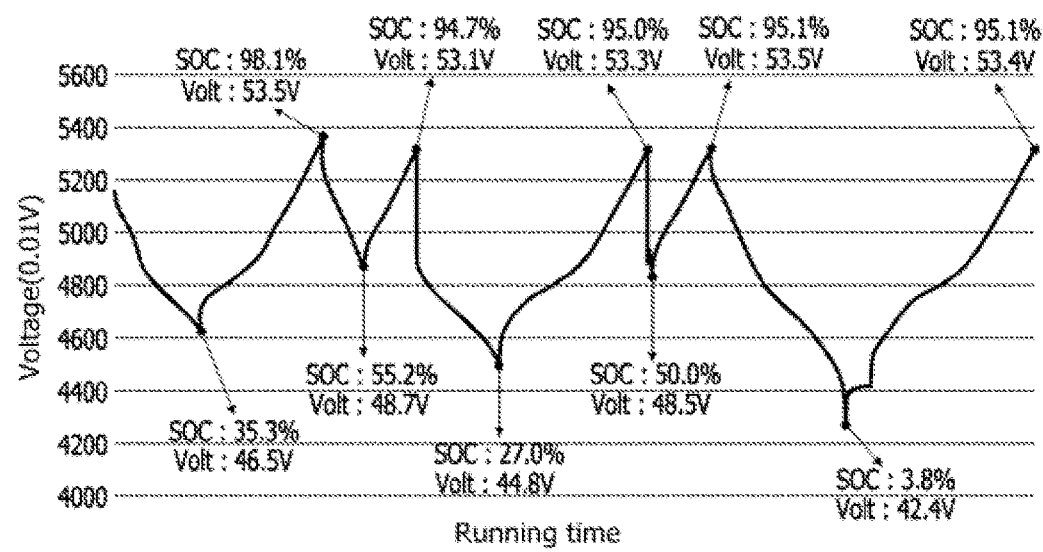
FIG. 10 is an exemplary view showing a test result for verifying the SOC calculation result, according to an embodiment of the present invention.
Figure 11:
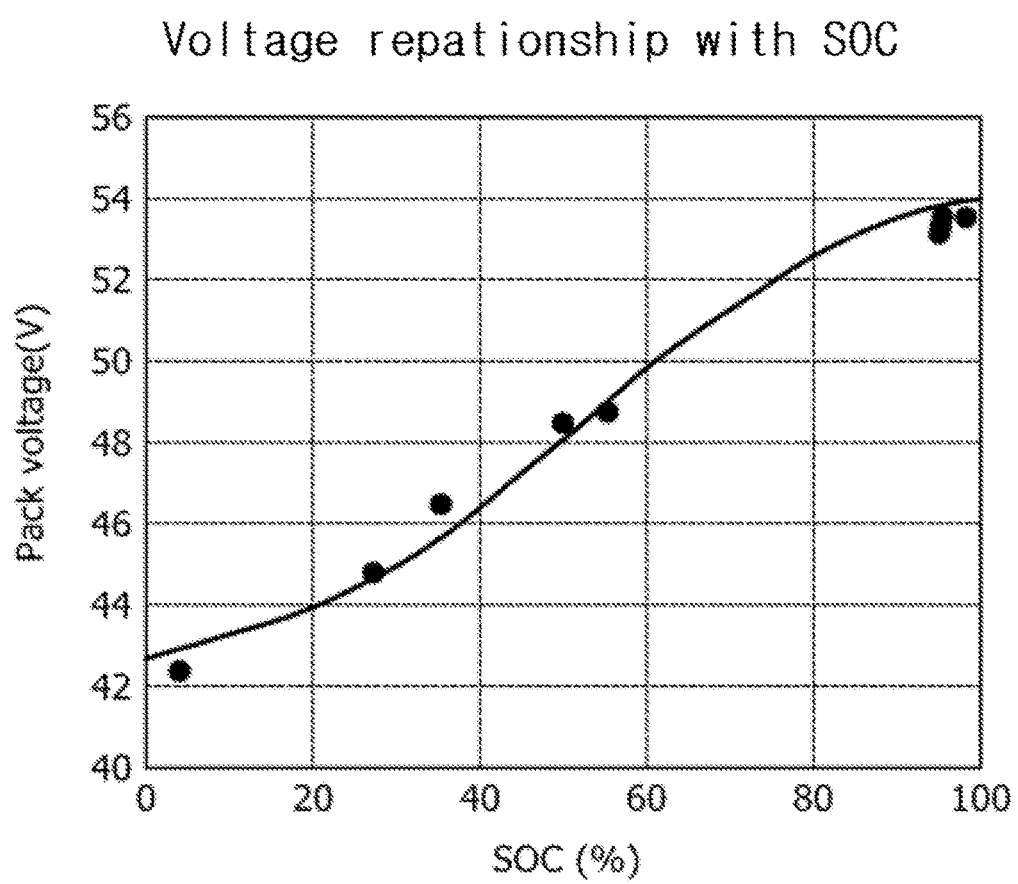
FIG. 11 is an exemplary view showing a relationship between the SOC and the OCV of the battery pack, according to the test result of FIG. 10.

When the currently available battery capacity ratio (or cell capacity ratio) (%) is calculated as described above, the control unit calculates a currently available state of charge of the battery (or cell capacity) based on the currently available battery capacity ratio (or cell capacity ratio) (%) (S107) (see FIGS. 10 and 11).

FIG. 10 is an exemplary view showing a test result for verifying the SOC calculation result, according to an embodiment of the present invention, and FIG. 11 is an exemplary view showing a relationship between the SOC and the OCV of the battery pack, according to the test result of FIG. 10.

FIG. 10 is an exemplary view showing a result of a charging/discharging test of a battery pack in which one pack is comprised of 13 battery cells of 4.2V, wherein the charging/discharging conditions were set in a similar manner as the actual battery-usage conditions. It can be seen that the SOC that is calculated by the method according to the present embodiment and the measured voltage match a result of calculating the SOC by the OCV within an error range in FIG. 11 during the charging and discharging (here, the solid line of the graph follows the tendency of the regression analysis by the Boltzmann equation). That is, the solid line shown in the graph of FIG. 11 refers to the SOC that is calculated when an OCV value (the value that is measured when there is no load) is given, and the point (corresponding to the charging/discharging peak point of FIG. 10) shown in the graph of FIG. 11 refers to the SOC that is calculated in the test of FIG. 10 (the test in the actual load conditions). It can be seen that the SOC that is calculated in the state in which the actual load is connected according to the method of the present embodiment is equal to the SOC within an error range, which is calculated when the OCV value (the value that is measured when there is no load) is given.

Therefore, the control unit may predict a stable battery voltage (that is, a stable battery voltage after the lapse of the voltage stabilization time) by using the battery voltage that is measured in the state in which the actual load is connected (that is, in the discharged state), and may calculate and output the SOC by using the predicted stable battery voltage.

However, the currently available battery capacity (or cell capacity) may not be calculated in the present embodiment.

Referring back to FIG. 2, the control unit calculates the current SOH (or the available amount of discharge) (S108), and outputs the same through a specified information output unit (not shown) (S109).

Hereinafter, a method for calculating the current SOH (or the available amount of discharge) will be described.

For example, when the initial battery capacity ratio (or cell capacity ratio) is 100%, which is set to be the maximum value of the SOH, and when the current temperature (T) is 20 to 40 (° C.) and the amount of accumulated discharge is C, the amount of capacity reduction of the battery may be calculated by using Equation 4 with reference to FIG. 9. That is, the amount of capacity reduction may be calculated by multiplying the capacity reduction rate depending on the temperature by the amount of accumulated discharge (C).

$$\text{capacity reduction amount}=(0006*T+0.0036)*C \quad \text{[Equation 4]}$$

For example, if the amount of accumulated discharge of the battery is 600, which is used at 20° C., on the assumption that the full state of health (SOH) of the battery is 100%, it means that the state of charge of the battery decreases by 9.36%.

That is, since the temperature varies in the actual operation environment, the total amount of capacity reduction of the battery is calculated by applying the amount of accumulated discharge that is used in the corresponding temperature, and based on the same, a value that the state of health (SOH) of the battery reaches may be predicted to correspond to the amount of accumulated discharge when it is used at a constant temperature.

More specifically, in the case where the state of charge of the battery decreases by 9.36% when the amount of discharge (or the amount of accumulated discharge) is 600 at the usage temperature of 20° C. on the assumption that the initial battery capacity ratio (or cell capacity ratio) is 100% as described above, the currently available amount of discharge (SOH) of the battery may be 90.64%. If the state of charge of battery additionally decreases by 11.04% when the amount of discharge (or the amount of accumulated discharge) is 400 at 40 (° C.) as the temperature further varies, the currently available amount of discharge (SOH) of the battery may be 79.6%. In addition, if the state of charge of battery additionally decreases by 4.32% when the amount of discharge (or the amount of accumulated discharge) is 200 at 30 (° C.) as the temperature further varies, the currently available amount of discharge (SOH) of the battery may be 75.28%.

In this state, if the battery continues to be used at 30 (° C.), the state of health (or the available amount of discharge) of the battery, which can be additionally used until the state of health (SOH) (or the available amount of discharge) of the battery reaches a predetermined value (for example, 50%), may be 25.28%, and the available amount of discharge (or the SOH) may be calculated by using Equation 4 as follows.

$$25.28 = (0.0006*30 + 0.0036)*C \qquad (1)$$

$$C = \frac{25 \cdot 28}{0.0006*30 + 0.0036} \approx 1170.37 \qquad (2)$$

That is, the available amount of discharge (or SOH) may be predicted to be 1170.

As described above, the present embodiment enables the prediction of the state of health (SOH) of the battery in consideration of the usage temperature of the battery in the current usage environment of the rechargeable battery so that the user can be aware of the battery replacement timing in advance and can appropriately manage the same.

While the present invention has been described above with reference to the embodiments shown in the drawings, they are illustrative only, those skilled in the art will understand that various modifications and other equivalent embodiments may be made without departing from the spirit and the scope of the present invention. Therefore, the scope of protection of the present invention should be defined by the appended claims.

What is claimed is:

1. A method for predicting battery health in consideration of a temperature of a battery management system, the method comprising:

measuring a voltage, current, and temperature of a battery and calculating an initial state of charge of the battery by a control unit when an operation of the battery management system is started;

checking whether the battery is in a charged state or in a discharged state by the control unit;

calculating a current amount of accumulated discharge by the control unit if the battery is in the discharged state;

calculating an accumulated discharge rate capacity by the control unit if the battery is in the charged state and if the current amount of accumulated discharge is calculated;

calculating a capacity reduction rate of the battery depending on the temperature of the battery by the control unit;

calculating a currently available battery capacity ratio by using the capacity reduction rate; and calculating and outputting a state of health of the battery, which correlates to the temperature of the battery, by the control unit based on the currently available battery capacity ratio, wherein, when an initial value of a battery capacity ratio is set to be 100%, which is a maximum value of the state of health of the battery, and when the current amount of accumulated discharge corresponding to the temperature is C1, the calculating of the currently available battery capacity ratio further comprises:

calculating an amount of capacity reduction for the temperature by multiplying the capacity reduction rate of the battery and the current amount of accumulated discharge, using a following equation: the amount of capacity reduction=(second coefficient*T+second constant)*C1;

calculating a first available battery capacity ratio by subtracting the amount of capacity reduction for the temperature from the maximum battery state of health of 100%; and calculating the currently available battery capacity ratio by subtracting a predetermined reference amount of ratio from the calculated first available battery capacity ratio, wherein the calculating of the state of health of the battery further comprises:

applying the currently available battery capacity ratio to the following equation: the currently available battery capacity ratio=(second coefficient*T+second constant) *C2; and calculating C2 that is a final available amount of discharge that is the remaining state of health of the battery, and wherein the battery is replaced when the remaining state of health of the battery reaches a predetermined level.

2. The method according to claim 1, wherein the initial state of charge of the battery is calculated based on a relationship between an open circuit voltage and the state of charge according to a voltage stabilization time, and is calculated based on the voltage that is measured in a state after a lapse of the voltage stabilization time or in an initial state in which a load is not operated.

3. The method according to claim 2, wherein the voltage stabilization time refers to a time taken for a voltage change to be stable in a state in which a discharge of the battery is completely stopped, and is determined according to whether or not a voltage change value reaches a predetermined voltage change value or less.

4. The method according to claim 1, wherein the accumulated discharge rate capacity refers to a ratio of a current state of charge of the battery according to the amount of accumulated discharge to the initial state of charge of the battery, and is calculated by dividing the current state of charge of the battery according to the current amount of accumulated discharge by the initial state of charge of the battery.

* * * * *